United States Patent
McIntosh et al.

(10) Patent No.: US 6,679,909 B2
(45) Date of Patent: Jan. 20, 2004

(54) RAPID EXCHANGE DELIVERY SYSTEM FOR SELF-EXPANDING STENT

(75) Inventors: Winnette S. McIntosh, Sunnyvale, CA (US); Christopher J. Tarapata, North Andover, MA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 150 days.

(21) Appl. No.: 09/919,490

(22) Filed: Jul. 31, 2001

(65) Prior Publication Data

US 2003/0028235 A1 Feb. 6, 2003

(51) Int. Cl.[7] .................................................. A61F 2/06
(52) U.S. Cl. ................................. 623/1.11; 604/103.09
(58) Field of Search ........................... 604/264, 103.04, 604/102.02, 524; 623/1.11, 1.23; 606/194, 191–193, 195–198; 600/43–435, 585

(56) References Cited

U.S. PATENT DOCUMENTS

| | | | |
|---|---|---|---|
| 3,856,190 A | * 12/1974 | Mole et al. .................... 223/94 |
| 4,748,982 A | 6/1988 | Horzewski et al. | |
| 5,061,273 A | 10/1991 | Yock | |
| 5,156,594 A | 10/1992 | Keith | |
| 5,180,368 A | 1/1993 | Garrison | |
| 5,195,978 A | 3/1993 | Schiffer | |
| 5,279,562 A | 1/1994 | Sirhan et al. | |
| 5,360,401 A | 11/1994 | Turnland | |
| 5,389,087 A | 2/1995 | Miraki | |
| 5,458,613 A | * 10/1995 | Gharibadeh et al. ......... 606/194 |
| 5,516,336 A | 5/1996 | McInnes et al. | |
| 5,533,968 A | 7/1996 | Muni et al. | |
| 5,545,134 A | * 8/1996 | Hilaire et al. .......... 604/103.04 |
| 5,567,203 A | 10/1996 | Euteneuer et al. | |
| 5,571,094 A | 11/1996 | Sirhan | |
| 5,656,013 A | * 8/1997 | Yoon ........................... 606/190 |
| 5,743,874 A | 4/1998 | Fischell et al. | |
| 5,743,875 A | 4/1998 | Sirhan et al. | |
| 5,807,355 A | 9/1998 | Ramzipoor et al. | |
| 5,823,995 A | 10/1998 | Fitzmaurice et al. | |
| 5,993,460 A | 11/1999 | Beitelia et al. | |
| 6,077,295 A | 6/2000 | Limon et al. | |
| 6,143,021 A | 11/2000 | Staehle | |
| 6,165,167 A | * 12/2000 | Delaloye ................ 604/103.04 |
| 6,179,810 B1 | 1/2001 | Wantink et al. | |
| 6,190,358 B1 | 2/2001 | Fitzmaurice et al. | |
| 6,193,686 B1 | 2/2001 | Estrada et al. | |
| 6,248,122 B1 | 6/2001 | Klumb et al. | |
| 6,273,899 B1 | 8/2001 | Kramer | |
| 6,290,673 B1 | * 9/2001 | Shanley .................. 604/102.02 |
| 6,299,595 B1 | 10/2001 | Dutta et al. | |
| 6,475,187 B1 | * 11/2002 | Gerberding ............ 604/103.09 |

FOREIGN PATENT DOCUMENTS

WO WO 01/43664 A1 6/2001

* cited by examiner

*Primary Examiner*—Julian W. Woo
*Assistant Examiner*—Tan-Uyen T. Ho
(74) *Attorney, Agent, or Firm*—Fulwider Patton Lee & Utecht, LLP

(57) ABSTRACT

A catheter assembly is provided having an inner member and an outer member extending along a longitudinal axis, the inner member and the outer member having a coaxial configuration and dimensioned for relative axial movement. The outer member has a wall defining an opening such as a longitudinal slot; an expanding member such as a leaf spring is connected to the inner member, the leaf spring being adapted to engage with the longitudinal slot so as to maintain rotational alignment between inner member and outer member.

68 Claims, 7 Drawing Sheets

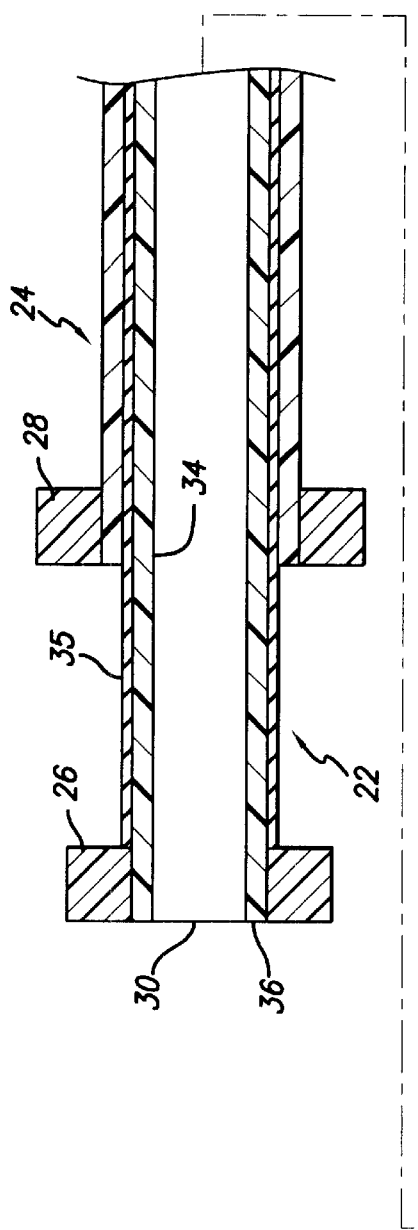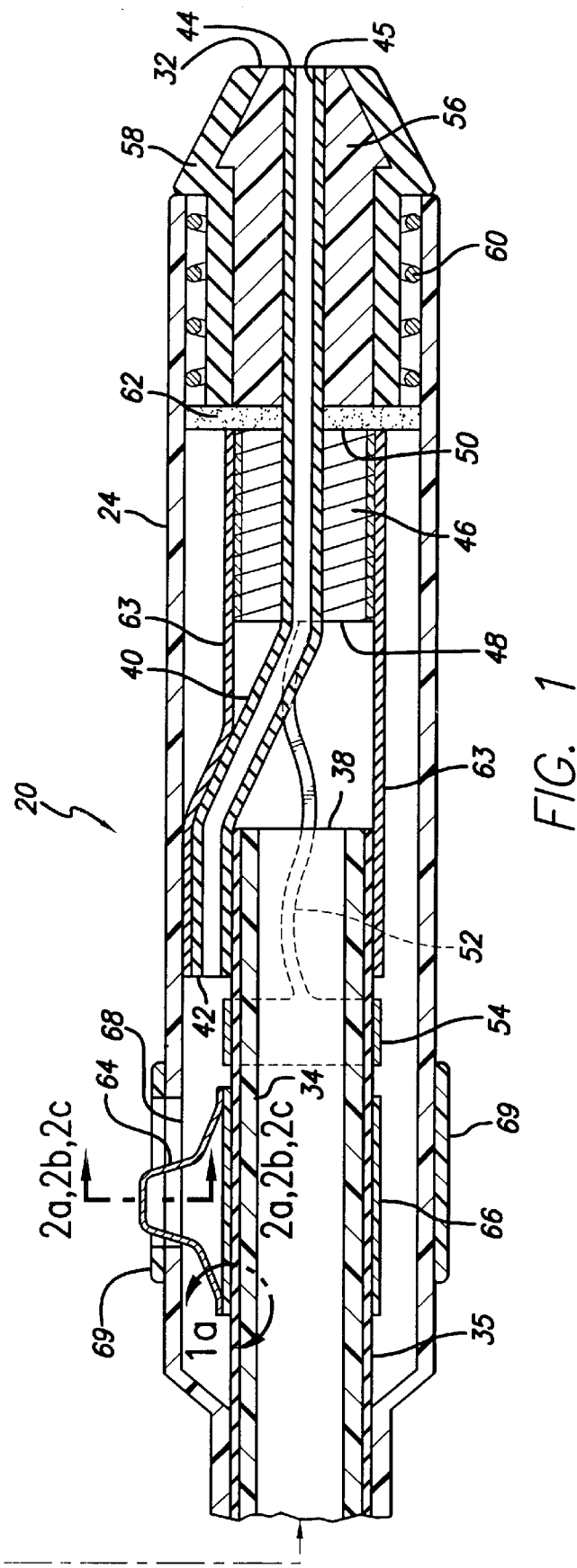

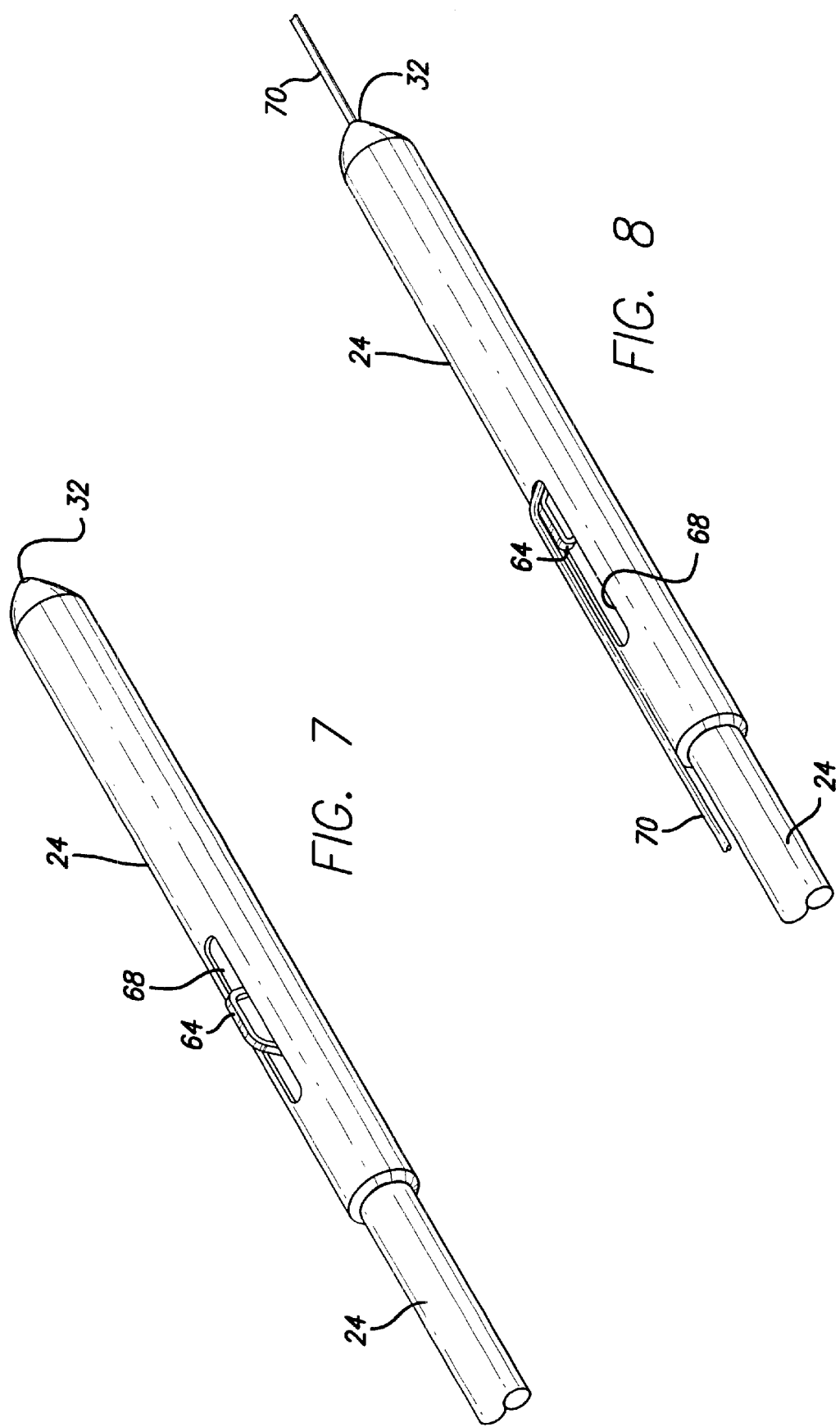

RAPID EXCHANGE DELIVERY SYSTEM FOR SELF-EXPANDING STENT

BACKGROUND OF THE INVENTION

The invention relates to stent delivery systems, which are used to implant a stent into a patient's body lumen to maintain the patency thereof. The stent delivery system is useful in the treatment and repair of body lumens, including coronary arteries, renal arteries, carotid arteries, and other body lumens.

Stents are generally cylindrically-shaped devices which function to hold open and sometimes expand a segment of a blood vessel or other body lumen. They are particularly suitable for use to support and hold back a dissected arterial lining which can occlude the fluid passageway therethrough. Stents also are useful in maintaining the patency of a body lumen, such as a coronary artery, after a percutaneous transluminal coronary angioplasty (PTCA) procedure or an atherectomy procedure to open a stenosed area of the artery.

Typically, a stent is delivered intraluminally through a percutaneous incision through the femoral or renal arteries. The stent is mounted on the distal end of an elongated catheter and the catheter and stent are advanced intraluminally to the site where the stent is to be implanted. A variety of devices are known in the art for use as stents and have included coiled wires in a variety of patterns that are expanded after being placed intraluminally. Three different approaches for expanding stents have been developed in the art, namely, balloon expanded stents, elastically self-expanding stents, and heat expanded stents. Balloon expanded stents are placed over a deflated balloon mounted on the catheter. The balloon is then inflated to expand the stent radially outwardly into contact with the arterial wall, whereupon the stent undergoes plastic deformation and remains in an expanded state to hold open and support the artery. Elastically self-expanding stents are adapted to be delivered in an elastically compressed state while confined within an outer restraining sheath, but to elastically expand when the sheath is removed and to provide support to the vessel within which it is implanted. Heat expanded stents are made from heat-sensitive materials such as nickel-titanium, are cooled in a compressed shape before insertion into the patient, but assume a pre-existing expanded shape when exposed to the body temperature of a patient.

With respect to self-expanding stents, typically a retractable sheath is positioned over the self-expanding stent which is mounted on the distal end of the catheter. Once the catheter has been advanced intraluminally to the site where the stent is to be implanted, the sheath is withdrawn thereby allowing the self-expanding stent to expand radially outwardly into contact with the arterial wall, thereby holding open and supporting the artery. Both balloon expanded stents and heat sensitive self-expanding stents may also be delivered within a retractable sheath, similar to that used with a self-expanding stent. In such cases the sheath may function to secure the stent on the catheter during insertion or to prevent sharp edges of the stent from tearing at the wall of the lumen during insertion.

One embodiment of a catheter delivery system is the so-called "over-the-wire" delivery system, in which a catheter is introduced into the patient over a guide wire which has been previously introduced. In this embodiment, the guide wire runs within a lumen extending the entire length of the catheter. Another embodiment of the catheter delivery system is the so-called "rapid exchange" delivery system, in which the guide wire runs within a lumen in the catheter extending from the distal tip of the catheter to a point just proximal of where the stent is positioned on the catheter, at which point the lumen terminates on the outside of the catheter and the guide wire emerges from the catheter to extend proximally, outside of the catheter. Thus, the catheter of a "rapid exchange" delivery system has a guide wire lumen port at the distal end of the catheter, and a proximal port spaced a relatively short distance from the distal end and a relatively long distance from the proximal end of the catheter. This "rapid exchange" configuration allows the surgeon to rapidly and single-handedly place the delivery system over the guide wire or to exchange one delivery system for another, because the length of the guide wire lumen in the catheter is much shorter than used in an over-the-wire delivery system.

One of the problems associated with the prior art catheter-delivery systems which use a retractable outer sheath is that the addition of a retractable sheath tends to reduce the overall flexibility of the delivery system. Another problem is that, in the case of the rapid exchange delivery system, the addition of a retractable sheath to surround the catheter introduces a problem of rotational alignment between the sheath and the catheter. Upon commencement of installing the delivery system over the guide wire, the surgeon must introduce the proximal tip of the guide wire into the catheter lumen at the distal tip of the catheter. The surgeon then advances the guide wire proximally through the catheter lumen until the proximal tip of the guide wire emerges from the catheter and protrudes through an opening in the wall of the sheath. If, during the foregoing process, the sheath rotates relative to the catheter, the surgeon may have difficulty in aligning the opening with the guide wire tip, so as to get the guide wire tip to protrude from the opening. This complication can be a major problem for the surgeon to resolve under the pressure of surgery.

Thus, there has been found in the art a need for a reliable rapid-exchange stent delivery system for a self expanding stent, in which rotational alignment between the outer sheath and the catheter may be maintained prior to and during the process of positioning the delivery system over the guide wire. Further, the art has found a need for a delivery system for a self expanding stent which has improved flexibility characteristics. The present invention addresses these and other needs.

SUMMARY OF THE INVENTION

The present invention is directed to a catheter delivery system having improved flexibility characteristics. In a further aspect, the invention is directed to a rapid-exchange catheter delivery system having an outer sheath, in which the sheath is held in rotational alignment with the catheter prior to and during the process of positioning the delivery system over a guide wire. Means for maintaining such rotational alignment may assume the form of a leaf-spring or other expanding member attached to the catheter and adapted to protrude through a slot or opening defined in the sheath.

A catheter assembly for removably attaching an intravascular stent is provided in which an elongated catheter has an inner member and an outer member extending along a longitudinal axis wherein the inner member and the outer member have a coaxial configuration and are dimensioned for relative axial movement. A self-expanding stent, having an open lattice structure, and being adapted to be expandable to an open configuration, is mounted on the inner member, within the outer member.

The present invention includes a leaf spring, attached to the inner member, which engages with a slot on the outer member so as to maintain the inner member and the outer member in rotational alignment. The leaf spring is adapted to deflect radially inwardly and to disengage from the slot in the outer member, either after the distal tip of a guide wire is extended from within the outer member over the leaf-spring outwardly through the slot in the outer member, or when the outer member is proximally withdrawn relative to the inner member.

In a further aspect of the invention, the distal end of the inner member is configured as a helical coil to enhance the overall flexibility of the delivery assembly.

The invention also includes a method of implanting a self-expanding stent utilizing the catheter-delivery system described above. Using the catheter-delivery system, a guide wire is proximally advanced through a lumen of the delivery system from the distal end until it encounters the leaf-spring, whereupon the guide wire is deflected outwards through the slot. The leaf spring is deflected radially inwardly and disengages from the slot in the outer member when the outer member is proximally withdrawn relative to the inner member.

The invention also relates to a method of assembling the delivery system described above. The method includes inserting the ends of the leaf spring through the wall of a tubular sleeve so that the ends are positioned within the lumen and the center portion of the leaf-spring is positioned outside the lumen of the sleeve. The sleeve is then slid over the inner member to a desired position on the inner member. The sleeve may be attached by friction fit, adhesive, or laser welding.

Other features and advantages of the present invention will become more apparent from the following detailed description of the invention, when taken in conjunction with the accompanying exemplary drawings.

BRIEF DESCRIPTION OF THE DRAWINGS

FIG. 1 is a sectional view of a stent delivery system embodying features of the present invention.

FIG. 1a is a detail view of an aspect of FIG. 1, showing an embodiment of how the leaf-spring mechanism may be positioned relative to the inner member.

FIG. 7 is a perspective view of an aspect of the stent delivery system exemplified in FIG. 1.

FIG. 8 is a perspective view of an aspect of the stent delivery system exemplified in FIG. 6.

DETAILED DESCRIPTION OF THE PREFERRED EMBODIMENTS

Figure 2A:
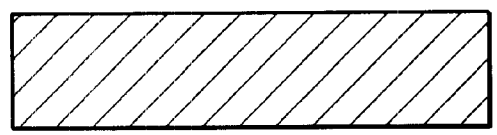
FIGS. 2a, 2b and 2c are sectional views exemplifying embodiments of the leaf-spring mechanism embodying features of the present invention.

The present invention relates to a rapid exchange delivery catheter system in which a stent is delivered intraluminally into a human patient's body lumen, such as a coronary artery, carotid artery, renal artery, peripheral artery and veins, and the like. The invention provides for a stent delivery catheter assembly, a method of assembly, and a method of use in which a stent is implanted in a patient. In one aspect, the invention is directed to a rapid-exchange catheter delivery system having an outer sheath, in which the sheath is held in rotational alignment with the catheter prior to and during the process of positioning the delivery system over a guide wire. Means for maintaining such rotational alignment may assume the form of a leaf-spring or other expanding member attached to the catheter and adapted to protrude through a slot or opening defined in the sheath.

There are numerous prior art stent delivery systems which may be used in conjunction with the present invention. The stent delivery systems suitable for use with the present invention are "rapid exchange" delivery systems which have an outer sheath adapted to slide over an inner sheath so as to cover a stent. The invention described in detail herein is described in the context of an elastically self-expanding stent delivery system. However, the invention is not limited to such use, and may equally be used with a delivery system for a balloon expanded stent or heat expanded stent.

In one embodiment of the invention, as exemplified in FIG. 1, a rapid exchange catheter assembly 20 is provided to deliver and implant a stent. Rapid-exchange catheters are known in the art and details of the construction and examples of use are set forth in U.S. Pat. Nos. 5,458,613; 5,346,505; and 5,300,085. Rapid exchange catheter assembly 20 incorporates an inner member 22 and an outer member 24 arranged in coaxial alignment. Inner member 22 is slidably positioned within outer member 24 and relative axial movement between the two members is provided by inner member control handle 26 and outer member control handle 28. The control handles 26, 28 can take numerous forms, but are depicted schematically for ease of illustration. As an example, however, control handles 26, 28 can take the form of a thumb-switch arrangement, a rotating-screw-type arrangement, or a ratcheting arrangement. Such control handle means are well known in prior art catheter-delivery systems.

Inner member 22 has a proximal end 30 and a distal end 32. Inner member comprises a catheter 34 which has proximal end 36 and distal end 38. The catheter 34 may be surrounded by a first jacket 35, adapted to lend lubricity to the inner member. Inner member further comprises a guide wire lumen 40, having proximal end 42 and distal end 44. As exemplified in FIG. 1, guide wire lumen 40 is configured to extend distally, from its proximal end 42 which is positioned adjacent to catheter 34 and just proximal of the distal end 38 thereof, to its distal end 44 which is located at the distal end 32 of the inner member. The profile of the guide wire lumen 40 extends distally along and adjacent the catheter 34, and then deflects from being adjacent to the catheter so as to extend coaxially therewith. Guide wire lumen 40 terminates in a distal opening 45 at its distal end 44.

Figure 3:
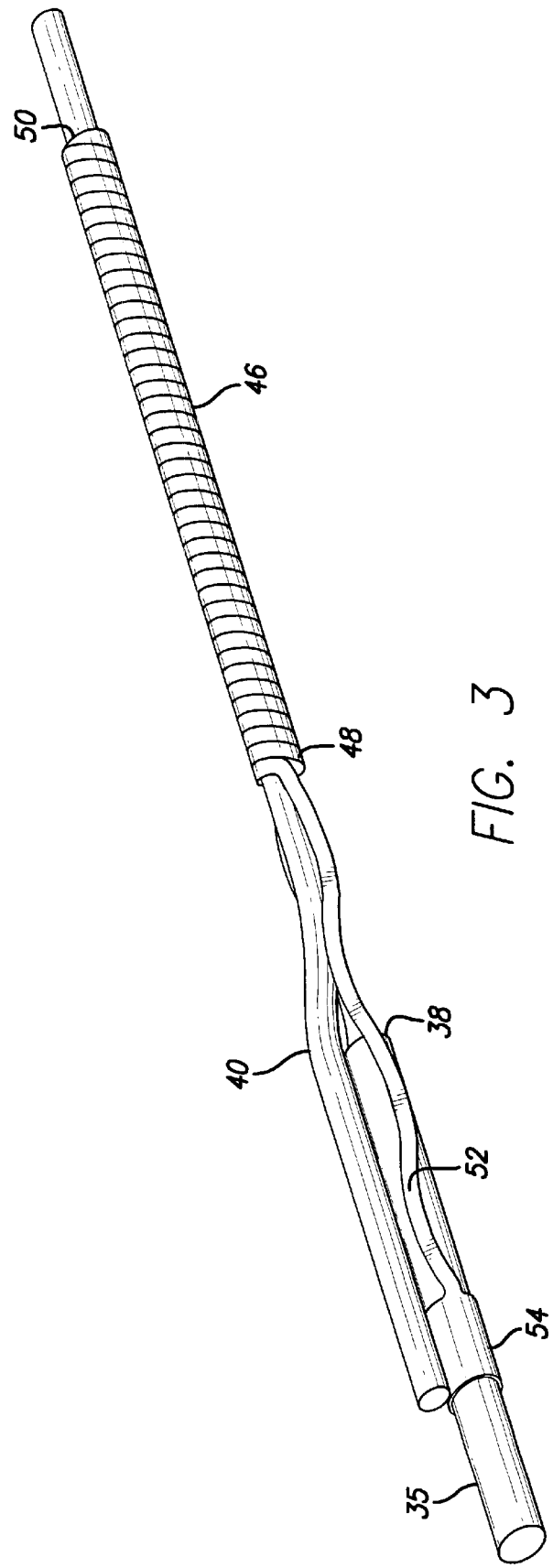
FIG. 3 is a perspective view of an aspect of the stent delivery system of FIG. 1.

Inner member 22 further includes a helical coil 46 having a proximal end 48 and a distal end 50. The helical coil may be positioned surrounding the guide wire lumen 40 at a location on the guide wire lumen where it extends coaxially with the catheter 34. As exemplified in FIG. 3, the helical coil 46 may be connected to the catheter 34 by means of flexible arms 52 which extend from the coil to a ring 54 surrounding the catheter 34 and crimped onto the catheter. Preferably, the helical coil, arms, and rings may be laser cut from a single tubular metallic structure. The arms are adapted to transfer axial force from the catheter 34 to the helical coil 46. It will be appreciated that the helical coil 46 provides a degree of stiffness to the inner member at a position where there is no catheter, while at the same time providing adequate flexibility.

With continued reference to FIG. 1, inner member 22 further comprises a distal tip 56 which surrounds the guide wire lumen 40 at the distal end 32 of the inner member, and is shaped to provide a low profile a traumatic end so as to facilitate movement of the delivery system through the patient's vasculature. A flexible protective layer 58 may cover the distal tip. A self expanding stent 60 in compressed state may be positioned about the distal tip 52, held in place by outer member 24. A blocking element 62 adapted to prevent proximal movement of the stent 60 relative to inner member 22 may be positioned between the distal tip 56 and the helical coil 46, and may also be adapted to act as a radio-opaque marker. In an alternative embodiment, the helical coil may extend all the way to the distal end 32 of the inner member, with the distal tip 56 adapted to accommodate the coil. A second protective jacket 63 may surround the coil 46, the guide wire lumen 40, and portion of the catheter 34, as exemplified in FIG. 1.

The outer member 24 is configured to surround the inner member 22, and may have a diameter at its distal end larger than at its proximal end in order to accommodate all the elements of the inner member. The self-expanding stent 60 in its compressed state is positioned around the distal tip 56 of the inner member 22 and is held in compressed state by the outer member 24. As exemplified in FIGS. 4–6, when the outer member is withdrawn proximally relative to the inner member, the stent 60 is permitted to assume its expanded state so as to support the body lumen within which it is implanted.

A further component of the inner member 22 is an expanding member such as a leaf spring 64. In one embodiment the leaf-spring may be attached to the catheter 34 via a cylindrical sleeve 66 adapted to fit onto the catheter at a position proximal of the proximal end 42 of the guide wire lumen 40. For purposes of assembly, the leaf-spring may be first attached to the cylindrical sleeve 66 by inserting the ends of the leaf-spring through the wall of the sleeve so that the central portion of the leaf-spring is positioned on the outside of the sleeve lumen while the ends of the leaf-spring are positioned within the sleeve lumen, as exemplified in FIG. 1a. The resulting combination may then be slid longitudinally over the catheter 34 to the desired position, as exemplified in FIG. 1. The sleeve may be fixed to the inner member either by adhesive, by heat welding, or by laser welding. Alternatively, the sleeve may be heated prior to sliding it over the inner member, so that, when cooled, a friction fit to the inner member is achieved. Once the leaf-spring 64 is fixed to the inner member, it is adapted to protrude into an opening such as a slot 68 formed in the wall of the outer member 24. In a further aspect, the leaf spring may also protrude beyond the slot so that a substantial portion of the leaf spring is positioned outside the outer member. It will be appreciated that when the leaf-spring protrudes into the slot it provides rotational alignment between the outer member and the inner member. By maintaining such rotational alignment, the ease with which a guide wire may be threaded through the delivery system 20 is greatly enhanced, as is explained more fully below. In one particular embodiment, the leaf-spring may be made of a material having highly elastic properties such as a nickel-titanium alloy including Nitinol, or a chromium-cobalt-nickel alloy including Elgiloy™ (manufactured and sold by Elgiloy of Elgin, Ill.), which will not readily lose its shape through plastic deformation should it be subjected to large strain. This quality is useful in that it has been found that, during assembly or storage of the delivery catheter 20, the leaf-spring 64 may be accidentally subjected to strains which might plastically deform or fracture a leaf-spring of similar proportions made of stainless steel.

In one embodiment, outer member 24 may be modified in that the perimeter of the slot 68 in the outer member may be reinforced by adding thereto a collar 69 formed of the same material as the outer member, so that the thickness of the outer member along the longitudinal edges of the slot is greater than the overall average thickness of the outer member. The collar may be connected to the outer member by adhesive or known heat or laser welding techniques. It will be appreciated that the ability of the outside catheter to resist bending is reduced in the vicinity of the slot, and thus accidental excessive bending at the location of the slot may cause the outer member to plastically deform and form a permanent kink along a longitudinal edge of the slot, which may render the delivery assembly unusable. Thus, reinforcement of the outer member in the vicinity of the slot as described above may reduce accidental damage of such kind. The slot itself may be cut into the outer member and the collar with a sharp edge, or, alternatively, by known means using laser.

Figure 2B:
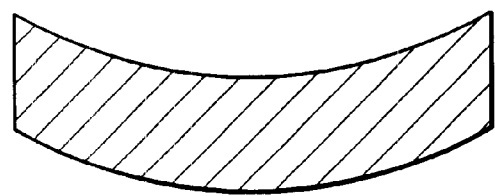
Figure 2C:
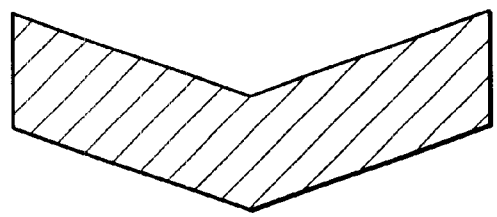
Figure 4:
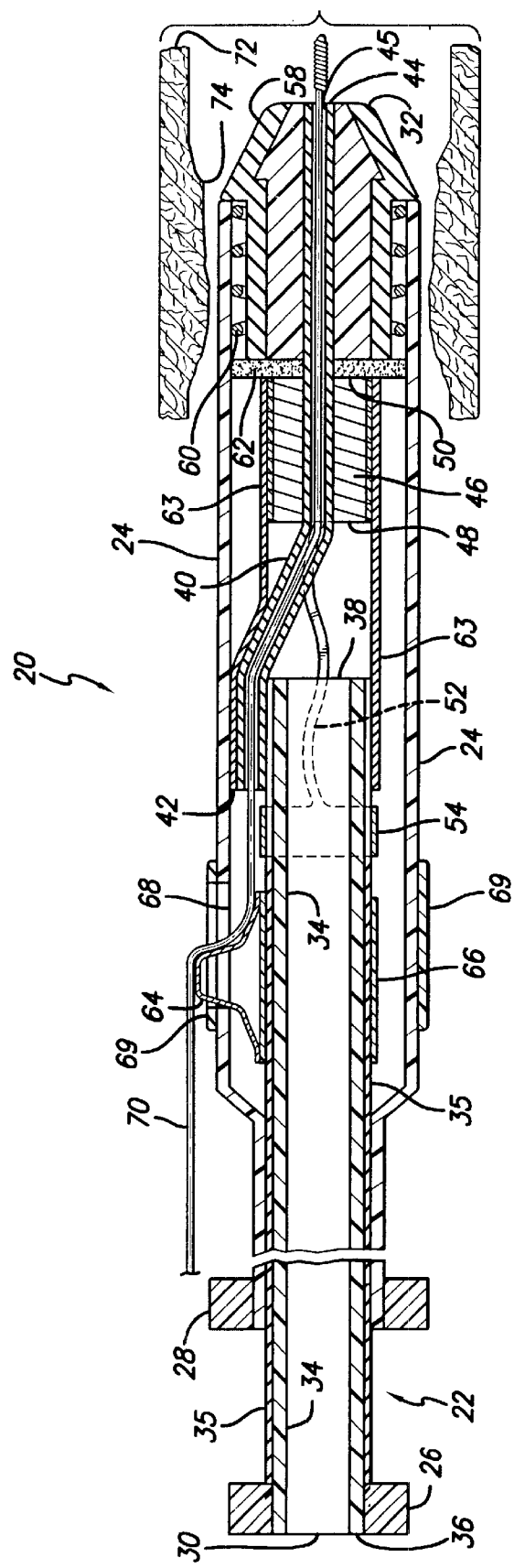
FIGS. 4 through 6 exemplify the stages of deploying a stent within a body lumen using a delivery system made in accordance with the present invention.
Figure 5:
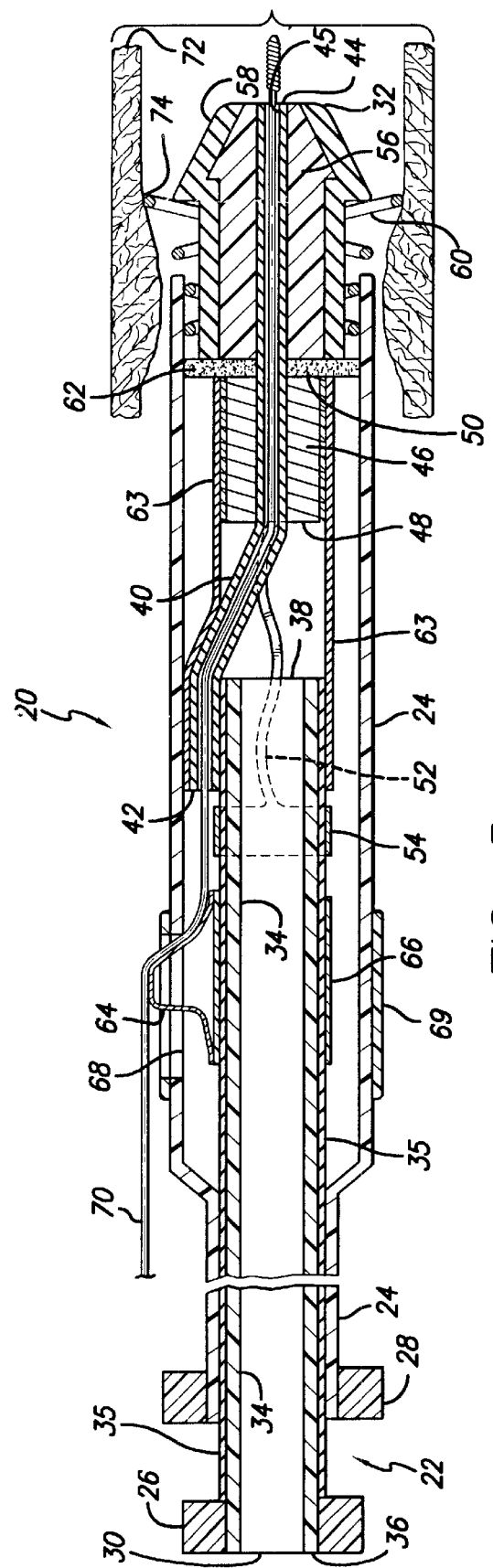
Figure 6:
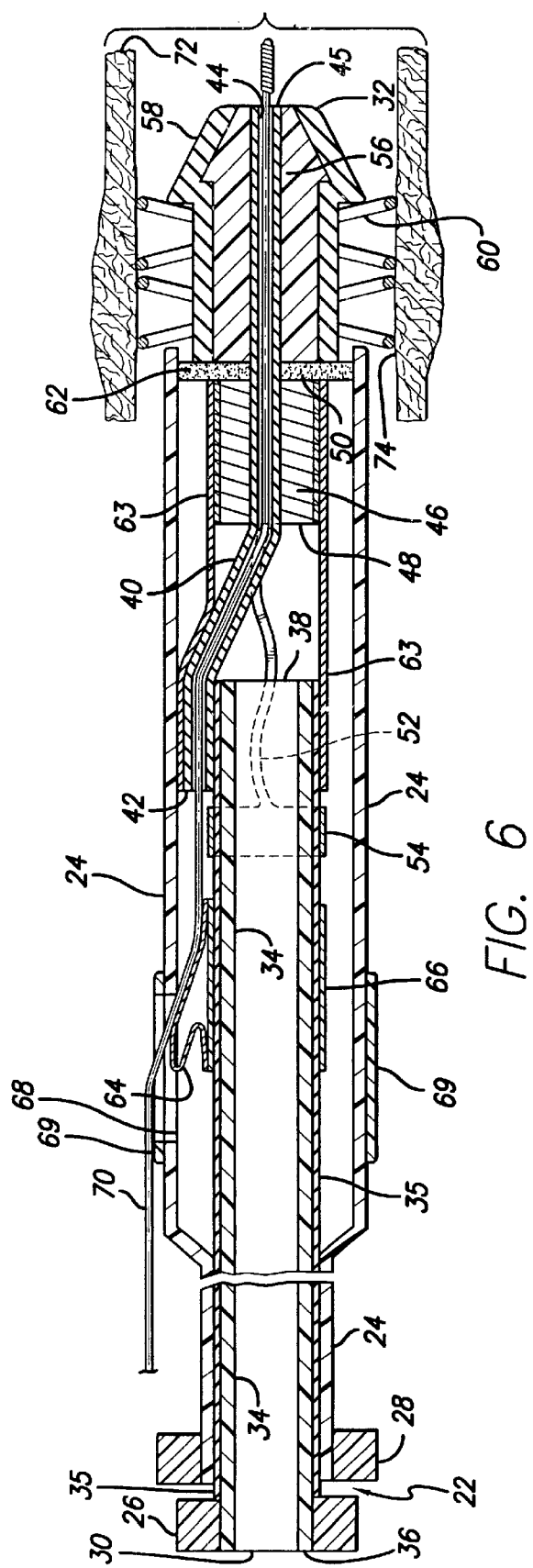

With reference to FIGS. 4–6, preparation for deploying a stent within a patient (not shown) using the delivery assembly of the present invention may commence using procedures which are well-known in the art, with the positioning of a guide wire 70 in the vasculature of the patient, after which the proximal tip (not shown) of the guide wire is left protruding from the patient. The proximal tip is then inserted in the distal opening 45 of the distal end 44 of the guide wire lumen 40 and threaded through the guide wire lumen until the proximal tip emerges from the proximal end 42 of the lumen. When the proximal tip of the guide wire is further advanced proximally from the proximal end 42 of the guide wire lumen, it may first contact the leaf-spring 64 and then deflect outwardly to emerge from the slot 68 in the outer member 24. It will be appreciated that within the catheter 20 there is a passageway for a guide wire extending between the distal opening 45 of the guide wire lumen 40 to the opening or slot 68. While the short cross section of the leaf-spring may be generally rectangular (FIG. 2a), in order to facilitate outward deflection of the guide wire the short cross sectional profile of the leaf-spring may depart from a rectangular shape, and may either have a generally "U" shape or a generally "V" shape as exemplified in FIGS. 2b and 2c. The leaf-spring may be adapted to remain engaged within the slot after the guide wire is advanced through the slot, as exemplified in FIG. 4, but to disengage at a later stage, as set forth below. The delivery system 20 is then advanced over the guide wire and its distal portion is inserted into the patient as required. In order to implant the self-expanding stent 60, the guide wire 70 is positioned in a patient's body lumen, at vessel wall 72, and typically guide wire 70 extends past a stenosed region 74. The catheter 20 is advanced along the guide wire until the stent 60 is positioned within stenosed region 74.

As exemplified in FIGS. 5 and 6, self-expanding stent 60 is implanted in stenosed region 74 by moving outer member 24 in a proximal direction, either while simultaneously moving inner member 22 in a distal direction or while holding it stationary relative to the patient. The leaf-spring 64 may be adapted to disengage from the slot when the outer member is moved proximally over the inner member, in that the outer member may depress the leaf-spring and, also, the outer member itself may slightly deform so as to pass over the leaf-spring. As portions of self-expanding stent 60 are no longer contained by outer member 24, the stent will expand radially outwardly into contact with the vessel wall 72 in the area of stenosed region 74. When fully deployed and implanted, as shown in FIG. 6, the stent 60 will support and hold open the stenosed region 74 so that blood flow is not restricted. It will be appreciated that, after the leaf-spring is disengaged from the slot and during proximal movement of the outer member 24 relative to inner member 22, the leaf-spring 64 represents no appreciable resistance to the movement of the outer member 24, as the leaf-spring is no longer engaged in the slot 68 of the outer member but may slide against the inner wall of the outer member. After stent 60 is implanted and contacts stenosed region 74, the catheter 20 and guide wire 70 are withdrawn from the patient's vascular system.

The stent as described herein can be formed from any number of materials, including metals, metal alloys and polymeric materials. Preferably, the stent may be formed from metal alloys such as stainless steel, tantalum, or the so-called heat sensitive metal alloys such as nickel titanium (NiTi). Stents formed from stainless steel or similar alloys typically are designed, such as in a helical coil or the like, so that they are spring biased outwardly.

With respect to all of the embodiments disclosed above, inner member 22 and outer member 24 can be formed from polymeric materials including polyurethanes, polyethylenes, polyethylterpthalate, and nylons. Similarly, sleeve 66 can be formed from polyurethane, elastomeric polyesters and the like. Generally speaking, the more proximal portions of inner member 22 and outer member 24 will be formed of a polymeric material that is stiffer than the distal section so that the proximal section has sufficient pushability to advance through the patient's vascular system. On the other hand, the more distal portion of inner member 22 and outer member 24 can be formed of a more flexible material so that the distal portion of the catheter will remain flexible and track more easily over the guide wire.

Other modifications and improvements may be made without departing from the scope of the invention. For example, the leaf spring is not limited to the shape exemplified in the drawings, but may be any expanding member and may assume any shape which expands to protrude through an opening or slot in the outer member. Accordingly, it is not intended that the invention be limited, except as by the appended claims.

What is claimed:

1. A catheter assembly comprising:
   an elongated catheter having an inner member and an outer member extending along a longitudinal axis, the inner member and the outer member having a coaxial configuration and dimensioned for relative axial movement, and wherein the outer member has a wall defining a longitudinal slot;
   a leaf spring connected to the inner member and being adapted to engage with the longitudinal slot so as to maintain rotational alignment between inner member and outer member.

2. The catheter assembly of claim 1 wherein the leaf-spring has opposing ends, further comprising a tubular sleeve defining a lumen, the ends of the leaf-spring being positioned within the sleeve lumen and the sleeve being positioned externally around and coaxially aligned with the inner member.

3. The catheter assembly of claim 2 wherein the sleeve is attached to the inner member by friction fit.

4. The catheter assembly of claim 2 wherein the sleeve is attached to the inner member by adhesive.

5. The catheter assembly of claim 2 wherein the sleeve is attached to the inner member by heat welding.

6. The catheter assembly of claim 2 wherein the sleeve is attached to the inner member by laser welding.

7. The catheter assembly of claim 1 wherein the leaf-spring is adapted to flexibly deform sufficiently to disengage from the slot and allow relative axial movement between inner member and outer member.

8. The catheter assembly of claim 1 wherein the leaf-spring is made of a nickel-titanium alloy.

9. The catheter assembly of claim 1 wherein the leaf-spring is made of a chromium-cobalt-nickel alloy.

10. The catheter assembly of claim 1 wherein the leaf-spring in short cross section is generally rectangular.

11. The catheter assembly of claim 1 wherein the leaf-spring in short cross section is generally non-rectangular.

12. The catheter assembly of claim 11 wherein the leaf-spring in short cross section is generally "V" shaped.

13. The catheter assembly of claim 11 wherein the leaf-spring in short cross section is generally "U" shaped.

14. The catheter assembly of claim 1 wherein the outer member has a wall, the thickness of the wall adjacent the longitudinal edges of the slot being greater than the average thickness of the wall over the length of the outer member.

15. The catheter assembly of claim 1 wherein the slot is formed in the outer member wall by laser cutting.

16. The catheter assembly of claim 1 wherein the slot is formed in the outer member wall by a sharp edge.

17. A method of implanting a stent in a body lumen comprising:
    selecting a delivery assembly having an inner member and an outer member extending along a longitudinal axis, the inner member and the outer member having a coaxial configuration and dimensioned for relative axial movement, and wherein the outer member defines a longitudinal slot and the inner member has a leaf spring adapted to engage with the longitudinal slot so as to maintain rotational alignment between inner member and outer member;
    inserting a guide wire into a lumen of the catheter; and
    advancing the guide wire through the lumen so that the guide wire encounters the leaf-spring and advances through the slot.

18. The method of claim 17 comprising the further step of sliding the outer member distally relative to the inner member.

19. The method of claim 18 wherein the catheter is so adapted that sliding the outer member distally relative to the inner member disengages the leaf-spring from the slot.

20. A method of assembling a delivery catheter having an inner member and an outer member extending along a longitudinal axis, the inner member and the outer member having a coaxial configuration and dimensioned for relative axial movement, and wherein the outer member defines a longitudinal slot and the inner member has a leaf spring adapted to engage with the longitudinal slot so as to maintain rotational alignment between inner member and outer member, comprising the steps:
    selecting a leaf spring with opposing ends separated by a center portion;
    selecting a tubular sleeve having a wall defining a lumen;
    inserting the ends of the leaf spring through the wall of the sleeve so that the ends are positioned within the lumen and the center portion of the leaf-spring is positioned without the lumen; and then
    sliding the sleeve over the inner member to a desired position on the inner member.

21. The method of claim 20 comprising the further step of fixing the sleeve to the inner member by laser welding.

22. The method of claim 20 comprising the further step of fixing the sleeve to the inner member by adhesive.

23. The method of claim 20 comprising the further step of fixing the sleeve to the inner member by heat welding.

24. The method of claim 20 comprising the further step of heating the sleeve prior to sliding it over the inner member so as to achieve a friction fit between sleeve and inner member.

25. A catheter assembly comprising:
an elongated catheter having an inner member and an outer member extending along a longitudinal axis, the inner member and the outer member having a coaxial configuration and dimensioned for relative axial movement, and wherein the outer member has a wall defining an opening;
an expanding member connected to the inner member and being adapted to engage with the opening so as to maintain rotational alignment between inner member and outer member.

26. The catheter assembly of claim 25 wherein the expanding member has opposing ends, further comprising a tubular sleeve defining a lumen, the ends of the expanding member being positioned within the sleeve lumen and the sleeve being positioned externally around and coaxially aligned with the inner member.

27. The catheter assembly of claim 26 wherein the sleeve is attached to the inner member by friction fit.

28. The catheter assembly of claim 26 wherein the sleeve is attached to the inner member by adhesive.

29. The catheter assembly of claim 26 wherein the sleeve is attached to the inner member by heat welding.

30. The catheter assembly of claim 26 wherein the sleeve is attached to the inner member by laser welding.

31. The catheter assembly of claim 25 wherein the expanding member is adapted to flexibly deform sufficiently to disengage from the opening and allow relative axial movement between inner member and outer member.

32. The catheter assembly of claim 25 wherein the expanding member is made of a nickel-titanium alloy.

33. The catheter assembly of claim 25 wherein the expanding member is made of a chromium-cobalt-nickel alloy.

34. The catheter assembly of claim 25 wherein the expanding member in short cross section is generally rectangular.

35. The catheter assembly of claim 25 wherein the expanding member in short cross section is generally non-rectangular.

36. The catheter assembly of claim 35 wherein the expanding member in short cross section is generally "V" shaped.

37. The catheter assembly of claim 35 wherein the expanding member in short cross section is generally "U" shaped.

38. The catheter assembly of claim 25 wherein the outer member has a wall, the thickness of the wall adjacent the edges of the opening being greater than the average thickness of the wall over the length of the outer member.

39. The catheter assembly of claim 25 wherein the opening is formed in the outer member wall by laser cutting.

40. The catheter assembly of claim 25 wherein the opening is formed in the outer member wall by a sharp edge.

41. A method of implanting a stent in a body lumen comprising:
selecting a delivery assembly having an inner member and an outer member extending along a longitudinal axis, the inner member and the outer member having a coaxial configuration and dimensioned for relative axial movement, and wherein the outer member defines an opening and the inner member has an expanding member adapted to engage with the opening so as to maintain rotational alignment between inner member and outer member;
inserting a guide wire into a lumen of the catheter; and
advancing the guide wire through the lumen so that the guide wire encounters the expanding member and advances through the opening.

42. The method of claim 41 comprising the further step of sliding the outer member distally relative to the inner member.

43. The method of claim 42 wherein the catheter is so adapted that sliding the outer member distally relative to the inner member disengages the expanding member from the opening.

44. A method of assembling a delivery catheter having an inner member and an outer member extending along a longitudinal axis, the inner member and the outer member having a coaxial configuration and dimensioned for relative axial movement, and wherein the outer member defines an opening and the inner member has an expanding member adapted to engage with the opening so as to maintain rotational alignment between inner member and outer member, comprising the steps:
selecting an expanding member with opposing ends separated by a center portion;
selecting a tubular sleeve having a wall defining a lumen;
inserting the ends of the expanding member through the wall of the sleeve so that the ends are positioned within the lumen and the center portion of the expanding member is positioned without the lumen; and
sliding the sleeve over the inner member to a desired position on the inner member.

45. The method of claim 44 comprising the further step of fixing the sleeve to the inner member by laser welding.

46. The method of claim 44 comprising the further step of fixing the sleeve to the inner member by adhesive.

47. The method of claim 44 comprising the further step of fixing the sleeve to the inner member by heat welding.

48. The method of claim 44 comprising the further step of heating the sleeve prior to sliding it over the inner member so as to achieve a friction fit between sleeve and inner member.

49. A catheter assembly comprising:
a. a catheter having
  i. a proximal end and a distal end;
  ii. a distal opening at the distal end;
  iii. a proximal opening spaced a relatively short distance from the distal end and a relatively long distance from the proximal end;
  iv. a passageway for a guide wire extending between the distal opening and the proximal opening;
  v. an inner member and an outer member extending along a longitudinal axis, the inner member and the outer member having a coaxial configuration and dimensioned for relative axial movement, wherein the outer member has a wall defining the proximal opening;
  vi. an expanding member connected to the inner member and being adapted to engage with the proximal opening so as to maintain rotational alignment between inner member and outer member.

50. The catheter assembly of claim 49 wherein the passageway is adapted to receive a guide wire inserted into the passageway, and to direct an end of the guide wire onto the expanding member.

51. The catheter assembly of claim 50 wherein the expanding member is adapted to deflect the end of the inserted guide wire through the proximal opening.

52. The catheter assembly of claim 49 wherein the outer member is adapted to deform the expanding member when the outer member is moved axially in relation to the inner member.

53. The catheter assembly of claim 49 wherein the expanding member is adapted in relation to the outer member to disengage from the proximal opening when the outer member is moved axially in relation to the inner member.

54. The catheter assembly of claim 49 wherein the expanding member has opposing ends, further comprising a tubular sleeve defining a lumen, the ends of the expanding member being positioned within the sleeve lumen and the sleeve being positioned externally around and coaxially aligned with the inner member.

55. The catheter assembly of claim 54 wherein the sleeve is attached to the inner member by friction fit.

56. The catheter assembly of claim 54 wherein the sleeve is attached to the inner member by adhesive.

57. The catheter assembly of claim 54 wherein the sleeve is attached to the inner member by heat welding.

58. The catheter assembly of claim 54 wherein the sleeve is attached to the inner member by laser welding.

59. The catheter assembly of claim 49 wherein the expanding member is adapted to flexibly deform sufficiently to disengage from the proximal port and allow relative axial movement between inner member and outer member.

60. The catheter assembly of claim 49 wherein the expanding member is made of a nickel-titanium alloy.

61. The catheter assembly of claim 49 wherein the expanding member is made of a chromium-cobalt-nickel alloy.

62. The catheter assembly of claim 49 wherein the expanding member in short cross section is generally rectangular.

63. The catheter assembly of claim 49 wherein the expanding member in short cross section is generally non-rectangular.

64. The catheter assembly of claim 63 wherein the expanding member in short cross section is generally "V" shaped.

65. The catheter assembly of claim 63 wherein the expanding member in short cross section is generally "U" shaped.

66. The catheter assembly of claim 49 wherein the outer member has a wall, the thickness of the wall adjacent the edges of the proximal opening being greater than the average thickness of the wall over the length of the outer member.

67. The catheter assembly of claim 49 wherein the proximal opening is formed in the outer member wall by laser cutting.

68. The catheter assembly of claim 49 wherein the proximal opening is formed in the outer member wall by a sharp edge.

* * * * *